United States Patent
Vieceli et al.

(10) Patent No.: US 11,891,600 B2
(45) Date of Patent: Feb. 6, 2024

(54) NUCLEIC ACID INDEXING TECHNIQUES

(71) Applicant: ILLUMINA, INC., San Diego, CA (US)

(72) Inventors: John S. Vieceli, Encinitas, CA (US); Ryan Matthew Kelley, San Diego, CA (US)

(73) Assignee: ILLUMINA, INC., San Diego, CA (US)

( * ) Notice: Subject to any disclaimer, the term of this patent is extended or adjusted under 35 U.S.C. 154(b) by 159 days.

(21) Appl. No.: 16/181,114

(22) Filed: Nov. 5, 2018

(65) Prior Publication Data

US 2019/0218545 A1 Jul. 18, 2019

Related U.S. Application Data

(60) Provisional application No. 62/582,175, filed on Nov. 6, 2017.

(51) Int. Cl.
 C12N 15/10 (2006.01)
 G16B 25/10 (2019.01)
 C12Q 1/6876 (2018.01)

(52) U.S. Cl.
 CPC ....... *C12N 15/1072* (2013.01); *C12Q 1/6876* (2013.01); *G16B 25/10* (2019.02)

(58) Field of Classification Search
 CPC .......................... C12N 15/1072; C12Q 1/6876
 See application file for complete search history.

(56) References Cited

U.S. PATENT DOCUMENTS

| | | |
|---|---|---|
| 6,172,218 B1 | 1/2001 | Brenner |
| 6,306,597 B1 | 10/2001 | Macevicz |
| 6,969,488 B2 | 11/2005 | Bridgham et al. |
| 7,001,792 B2 | 2/2006 | Sauer et al. |
| 7,057,026 B2 | 6/2006 | Barnes et al. |
| 10,081,807 B2 * | 9/2018 | Jacobson et al. .. C12N 15/1065 |
| 2005/0100900 A1 | 5/2005 | Kawashima et al. |
| 2006/0188901 A1 | 8/2006 | Barnes et al. |
| 2006/0240439 A1 | 10/2006 | Smith et al. |
| 2006/0281109 A1 | 12/2006 | Barr Ost et al. |
| 2007/0166705 A1 | 7/2007 | Milton et al. |
| 2009/0026082 A1 | 1/2009 | Rothberg et al. |
| 2009/0012758 A1 | 5/2009 | Rothberg et al. |
| 2010/0137143 A1 | 6/2010 | Rothberg et al. |
| 2010/0282617 A1 | 11/2010 | Rothberg |
| 2013/0079232 A1 | 3/2013 | Kain et al. |
| 2013/0137587 A1 * | 5/2013 | Van Eijk .................. C12Q 1/68 506/2 |
| 2013/0231253 A1 | 9/2013 | Amorese et al. |
| 2014/0141982 A1 | 5/2014 | Jacobson et al. |
| 2016/0017320 A1 | 1/2016 | Wang et al. |
| 2016/0122753 A1 | 5/2016 | Mikkelsen et al. |
| 2016/0314242 A1 | 10/2016 | Schnall-Lemin et al. |
| 2016/0319345 A1 | 11/2016 | Gnerre et al. |
| 2018/0033471 A1 | 11/2018 | Kelley et al. |

FOREIGN PATENT DOCUMENTS

| | | |
|---|---|---|
| WO | 2005/065814 A1 | 7/2005 |
| WO | 2011/100617 A2 | 8/2011 |
| WO | 2013142389 A1 | 9/2013 |
| WO | 2013163263 A2 | 10/2013 |
| WO | 2013181170 A1 | 12/2013 |
| WO | 2014062717 A1 | 4/2014 |
| WO | 2016/022833 A1 | 2/2016 |
| WO | 2016022833 A1 | 2/2016 |
| WO | 2017100441 A1 | 6/2017 |
| WO | 2018175997 A1 | 9/2018 |

OTHER PUBLICATIONS

Kircher et al. Supplementary Data (17 sheets) for "Double indexing overcomes inaccuracies in multiplex sequencing on the Illumina platform" (2011) Nucleic Acids Research, 40(1) pp. 1-8 (Year: 2011).*
Costello, M., et al., "Characterization and remediation of sample index swaps by non-redundant dual indexing on massively parallel sequencing platforms", BMC Genomics 19:322, May 8, 2018, 1-10.
Kircher, Martin, et al., "Double Indexing Overcomes Inaccuracies in Multiplex Sequencing on the Illumina Platform", Nucleic Acids Research, Oct. 21, 2011, (8 pages).
PCT/US18/59255, "Invitation to Pay Additional Fees, and Where Applicable, Protest Fee", dated Apr. 4, 2019, 1-6.
Kozich, J.J. et al.; "Development of a dual-index sequencing strategy and curation pipeline for analyzing amplicon sequence data on the MiSeq Illumina sequencing platform," Applied and Environmental Microbiology, vol. 79, No. 17, Sep. 2013, pp. 5112-5120.
Meyer, M. et al.; "Targeted high-throughput sequencing of tagged nucleic acid samples," Nucleic Acids Research, vol. 35, No. 15, Aug. 1, 2007, p. 97.
International Search Report and Written Opinion for PCT Application No. PCT/US2018/059255, dated Dec. 16, 2019, 22 pgs.
Kircher, et al., "Addressing challenges in the production and analysis of Illumina sequencing data", BCM Genomics, 12, 2011.
Meyer, M., et al., "Illumina sequencing library preparation for highly multiplexed target capture and sequencing", Cold Spring Harb Protoc 2010(6), Jun. 30, 2010, 1-20.
Singapore Application No. 11201911490U, Intellectual Property Office of Singapore Written Opinion, dated Oct. 28, 2020.
Cockroft, et al., "A single-molecule nanopore device detects DNA polymerase activity with single-nucleotide resolution", J. Am. Chem. Soc, 130(3), Jan. 23, 2008, 818-820.
Healy, Ken, "Nanopore-based single-molecule DNA analysis", Nanomed. 2(4), 2007, 459-481.

(Continued)

*Primary Examiner* — Nancy J Leith
*Assistant Examiner* — Jessica D Parisi
(74) *Attorney, Agent, or Firm* — Fletcher Yoder P.C.

(57) ABSTRACT

Presented herein are techniques for indexing of nucleic acid, e.g., for use in conjunction with sequencing. The techniques include generating indexed nucleic acid fragments from an individual sample, whereby the index sequence incorporated into each index site of the nucleic acid fragment is selected from a plurality of distinguishable of index sequences and such that the population of generated nucleic acid fragments represents each index sequence from the plurality. In this manner, the generated indexed nucleic acid fragments from a single sample are indexed with a diverse mix of index sequences that reduce misassignment due to index read errors associated with low sequence diversity.

19 Claims, 11 Drawing Sheets

(56) References Cited

OTHER PUBLICATIONS

Korlach, et al., "Selective aluminum passivation for targeted immobilization of single DNA polymerase molecules in zero-mode waveguide nanostructures", PNAS, vol. 105 No. 4, 2008, 1176-1181.
Levene, et al., "Zero-Mode Waveguides for Single-Molecule Analysis at high concentrations", Science 299, 2003, 682-686.
Lundquist, et al., "Parallel confocal detection of single molecules in real time", Opt. Lett. 33(9), 2008, 1026-1028.
Soni, et al., "Progress toward Ultrafast DNA Sequencing Using Solid-State Nanopores", Clin Chem, 53(11), 2007, 1996-2001.

* cited by examiner

FIG. 12

NUCLEIC ACID INDEXING TECHNIQUES

CROSS-REFERENCE TO RELATED APPLICATIONS

The present application claims priority to and the benefit of U.S. Provisional Application No. 62/582,175, filed Nov. 6, 2017, entitled "NUCLEIC ACID INDEXING TECHNIQUES," the disclosure of which is incorporated by reference in its entirety herein for all purposes.

BACKGROUND

The present disclosure relates generally to the field of data related to biological samples, such as sequence data. More particularly, the disclosure relates to techniques for indexing nucleic acids and resolving indexed sequences in acquired sequence data.

Genetic sequencing has become an increasingly important area of genetic research, promising future uses in diagnostic and other applications. In general, genetic sequencing involves determining the order of nucleotides for a nucleic acid such as a fragment of RNA or DNA. Next generation sequencing technology facilitates higher throughput sequencing using pooled sample preparations, e.g., multi-sample preparations. Within pooled sample preparations, each individual sample may be tagged or otherwise marked so that each sequencing read from the pooled sample may be associated with or attributed to an individual sample in the pool. However, the acquired sequence data may have errors and noise introduced from various sources, e.g., sample defects, sample preparation errors, and sequencing bias, which may decrease the accuracy of the associated sequence data to each individual sample. Therefore, it is desirable to develop methods for permitting high throughput sequencing in a multi-sample preparation with reduced attribution errors.

BRIEF DESCRIPTION

The present disclosure provides a novel approach for sample indexing of a biological sample. As provided herein, sample indexing is the process by which acquired sequencing reads are associated with a particular sample. In particular, the disclosed indexing technique does not introduce contamination between samples, works robustly with arbitrarily low numbers of samples (down to one for positive sample tracking), and supports even representation across multiplexed samples. The problems of index cross contamination, low-plex sample indexing performance, and variable index performance are solved with an indexing strategy that uses dual indexing per fragment to label each nucleic acid fragment prepared from a sample using a potential pool of multiple indices for the first and second index. The disclosed technique assigns a plurality of unique indices to each sample in both the first and second index, as opposed to the traditional combinatorial approach. In one embodiment, an index sequence is an exogenous nucleic acid sequence that may be incorporated into nucleic acids from a sample for sample identification and/or sample association. For example, the index sequences provided herein may be incorporated into nucleic acid fragments derived from samples of interest during sample preparation and/or during sequencing. Each index sequence has a distinguishable sequence relative to other index sequences used in the sequencing reaction. In certain embodiments, the index sequences are distinguishable from the endogenous nucleic acids of the sample or samples. The index sequences may be single or double-stranded, and may be at least 5 bases, at least 6 bases, at least 7 bases, at least 8 bases, or more. In certain embodiments, the index sequences are 5-8 bases, 5-10 bases, 5-15 bases, 5-25 bases, 8-10 bases, 8-12 bases, 8-15 bases, or 8-25 bases in length, etc.

The disclosed techniques provide indexed sequencing, whereby nucleic acid fragments derived from a particular sample are indexed using a pre-set pool of index sequences at each index site. While certain embodiments are disclosed in the context of two separate index sites per nucleic acid fragment (i.e., dual-indexing), it should be understood that the disclosed techniques may be used with nucleic acid fragments having at least one index site, at least two index sites, and that may incorporate three, four, or more index sites for each nucleic acid fragment. Indexed samples as provided herein may be pooled with other indexed samples for sequencing, provided that the other indexed samples are indexed with a different pool of index sequences at each index site. Accordingly, the present techniques permit pooled or multi-sample sequencing reactions whereby each individual sample in the sequencing reaction is indexed with an assigned unique set of index sequences, and the acquired sequencing reads are associated with the appropriate sample of origin via the assigned unique indexes.

The present techniques improve sequencing accuracy relative to techniques that incorporate a single index sequence per sample fragment and/or at each index site. For example, sequencing analysis may be performed using a rules-based assignment that discards any sequencing read that does not include an appropriate assigned index, e.g., at both the first and second index site for dual-indexed fragments or at just one index site for single-indexed fragments. The selected assigned indexes for each sample are designed to be diverse and distinguishable using a variety of sequencing techniques. For example, each index sequence has internal variability, variability within its assigned set, and variability relative to other index sequences assigned to other samples in the pool. In this manner, sequencing device errors at a single base read in the index are less likely because the diversity of the indices reduces misreads. In one example, if a sequencing run has low plexity or few samples, the index sequence data may nonetheless reflect a higher diversity than would be expected if the number of different index sequences at each index site had a 1:1 correspondence with the number of samples. That is, rather than using just a single index sequence per sample index site and whereby each sample is associated with only one index at each index site, which would yield such a 1:1 correspondence, each sample is instead associated with multiple potential index sequences at each index site. Accordingly, the different or distinguishable index sequences are present relative to a number of samples at a ratio of at least 2:1, at least 3:1, or at least 4:1 for each index site. In one example, for sequencing techniques that incorporate dedicated index reads (i.e., using an index primer targeting just upstream of the index sequence and sequencing a limited number of bases corresponding to the length of the index sequence), the present techniques and improved index diversity may result in more accurate base calling.

By increasing the accuracy of the index sequence data, fewer sequencing reads are discarded according to the rules-based assignment, which also improves the accuracy of sequencing even for low concentration samples and in cases of low sample number. Further, improved sample association via improved accuracy of index sequencing reduces the effects of index hopping (i.e., erroneous assignment of a sequencing read to a sample via index misidentification).

In one embodiment, a sample-indexed nucleic acid library preparation is provided that includes a first nucleic acid library prepared from a first sample, wherein the first nucleic acid library comprises a first plurality of nucleic acid fragments, wherein each nucleic acid fragment of the first plurality comprises at least two different index sequences selected from a first set of index sequences; a second nucleic acid library prepared from a second sample, wherein the second nucleic acid library comprises a plurality of nucleic acid fragments, wherein each nucleic acid fragment of the second plurality comprises at least two different index sequences selected from a second set of index sequences that are distinguishable from the first set of index sequences; and wherein the index sequences are arranged on individual nucleic acid fragments of the first plurality and second plurality such that a first index sequence of the index sequences is located 5' of a target sequence and a second index sequence of the index sequences is located 3' of the target sequence.

In another embodiment, a method for sequencing nucleic acid molecules is provided that includes the steps of providing a plurality of dual-indexed nucleic acid fragments generated from a sample, wherein each individual nucleic acid fragment of the nucleic acid fragments comprises a 5' adapter sequence, a 5' index sequence, a 3' adapter sequence, and a 3' index sequence, wherein a plurality of different 5' index sequences selected from a first set of 5' index sequences associated with the sample and a plurality of different 3' index sequences selected from a second set of 3 index sequences associated with the sample are represented in the dual-indexed nucleic acid fragments and wherein the plurality of different 5' index sequences and the plurality of different 3' index sequences are distinguishable from one another; generating sequencing data representative of sequences of the dual-indexed nucleic acid fragments; and associating an individual sequence of the sequences with the sample only when the individual sequence includes both the 5' index sequence selected from the first set and the 3' index sequence selected from the second set.

In another embodiment, a multi-sample library preparation kit is provided that includes a plurality of a nucleic acid fragments, each fragment comprising an index sequence and an adapter sequence. The plurality of nucleic acid fragments includes a first sample-associated nucleic acid fragment set comprising nucleic acid fragments having the index sequence selected from a first index set and wherein the adapter sequence is a first adapter sequence and comprising nucleic acid fragments having the index sequence selected from a second index set and wherein the adapter sequence is a second adapter sequence, and wherein each index sequences of first index set and the second index set is represented in the first sample-associated nucleic acid fragment set; and a second sample-associated nucleic acid set comprising nucleic acid fragments having the index sequence selected from a third index set and wherein the adapter sequence is a first adapter sequence and comprising nucleic acid fragments having the index sequence selected from a fourth index set and wherein the adapter sequence is a second adapter sequence, and wherein each index sequences of third index set and the fourth index set is represented in the second sample-associated nucleic acid fragment set; and wherein the first index set, the second index set, the third index set, and the fourth index set each comprise a plurality of index sequences distinguishable from one another.

In another embodiment, a sequencing substrate is provided that includes a plurality of nucleic acid capture sequences immobilized on a substrate, wherein each individual nucleic acid capture sequence comprises a first capture sequence complementary to a first adapter sequence or a second capture sequence complementary to a second adapter sequence. The sequencing substrate also includes a plurality of nucleic acid fragments coupled to respective nucleic acid capture sequences of the plurality of nucleic acid capture sequences, wherein the each individual fragment of the plurality of nucleic acid fragments comprises the first adapter sequence and the second adapter sequence and wherein each individual fragment of the plurality of nucleic acid fragments comprises a first sequence complementary to one index sequence of a first set of unique index sequences and a second sequence complementary to one index sequence of a second set of unique index sequences and wherein the first set of unique index sequences and the second set of unique index sequences are associated with only one sample from which the plurality of nucleic acid fragments are derived and wherein each unique index sequence of the first set and the second set is present in at least one nucleic acid fragment of the plurality of nucleic acid fragments.

In another embodiment, a method for sequencing nucleic acid molecules is provided that includes the steps of providing a plurality of dual-indexed nucleic acid fragments generated from a sample, wherein each individual nucleic acid fragment of the dual-indexed nucleic acid fragments comprises a sequence of interest derived from the sample, a 5' adapter sequence, a 5' index sequence, a 3' adapter sequence, and a 3' index sequence to generate dual-indexed nucleic acid fragments, wherein a plurality of different 5' index sequences selected from a first set of 5' index sequences associated with the sample and a plurality of different 3' index sequences selected from a second set of 3 index sequences associated with the sample are represented in the dual-indexed nucleic acid fragments and wherein the plurality of different 5' index sequences and the plurality of different 3' index sequences are distinguishable from one another; generating sequencing data representative of the sequence of interest; generating sequencing data representative of the 5' index sequence and the 3' index sequence; and assigning an individual sequence of interest to the sample only when the individual sequence of interest is associated with both the 5' index sequence selected from the first set and the 3' index sequence selected from the second set.

DRAWINGS

FIG. 12 shows an example of a graphical user interface in accordance with the present techniques.

DETAILED DESCRIPTION

Figure 1:
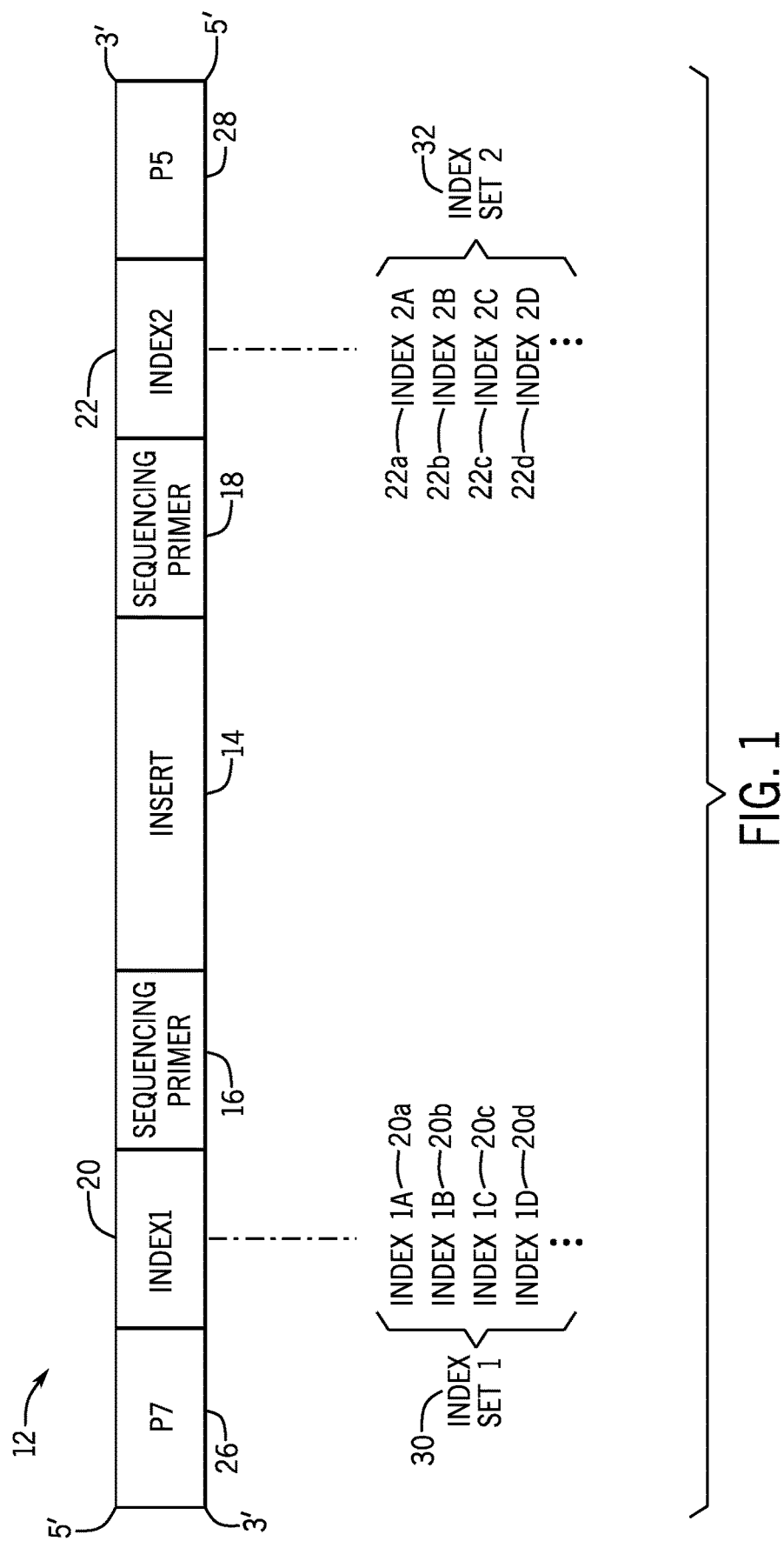
FIG. 1 is a schematic illustration of an index nucleic acid fragment in accordance with the present techniques.

The present techniques are directed to indexed nucleic acids and sequencing and analysis using the same. Sequencing of nucleic acids generates large amounts of raw data that is subsequently analyzed and compiled to provide meaningful information related to the sequenced sample. Sequencing techniques have advanced to process multiple samples simultaneously, which provides time and cost savings. However, such techniques present data processing challenges. The acquired sequencing data in a multi-sample sequencing run must be associated with its sample of origin before sequence assembly and analysis can be performed for each individual sample. However, often such sample association cannot be accurately completed using only the endogenous nucleic acid sequences. Accordingly, certain sequencing techniques incorporate a unique exogenous barcode or index sequence into the nucleic acids prior to sequencing, with each sample being associated with a unique barcode or index. After the sequencing data is acquired, sequence reads having the unique barcode or index are assigned to the appropriate sample of origin.

While such techniques facilitate assignment of multi-sample sequencing data, errors in sample assignment of sequencing reads still occur. Regardless of the source of the introduced sample assignment errors, sequence misassignments may result in inaccuracies in subsequent genome assembly and/or data analysis that is performed on misassigned data. If the index sequence data is not accurately acquired by a sequencing device, a sequencing read of a nucleic acid fragment (e.g., representative of a 50-300 bp nucleic acid fragment) may be assignment to the wrong sample on the basis of the inaccurate data. Further, certain sequencing techniques may be associated with a greater degree of index hopping or molecular recombination of indexes between samples. Index hopping may be caused by one end of this molecule (including the index region) tranferring between molecules in the template library. While index hopping may occur at a rate that is low (~0.05%), even low levels of index hopping may be relevant in a clinical context. In the case of a single index read, a transfer will result in the incorrect assignment of a sequencing read to another sample, which in turn will lead to contamination in downstream analysis. Index hopping may also occur with dual indexing using a combinatorial approach (e.g. assigning the same sequence to multiple samples in either index one or index two, but ensuring that any particular combination of index one and index two is unique to a specific sample). In certain embodiments, the present techniques are used in conjunction with unique indices within the first and second index reads. In that case, even if a swap occurs, the observed index combination will not be a member of the expected set of index pairs.

Provided herein are indexing techniques that result in reduced sequencing read misassignment. In contrast to techniques in which each sample is associated with a single barcode or index, the present techniques provide a plurality of index sequences that are uniquely associated with each individual sample and that are introduced during sample preparation. The plurality of index sequences are introduced at the index site (or index sites), such that individual nucleic acid fragments prepared from a sample have at least one index sequence and such that all of the different index sequences are present in a library of the nucleic acid fragments of each sample. In this manner, index sequence diversity on a per sample basis is introduced. This diversity may improve the accuracy of acquired index sequence data. In particular, sequencing devices that acquire image data representative of hundreds (or thousands) of nucleic acid fragments from two or more samples being simultaneously sequenced may have difficulty determining base calls when the samples lack nucleotide diversity, which in turn may result in acquired image data that is difficult to resolve. For example, certain sequencing techniques assess differences in image signal intensity to make base calls. For samples that only have a single index sequence per index site, the nucleotides at each sequencing cycle of the index sequence are as diverse as the total sample number, and may be insufficiently diverse for low sample number runs. Accordingly, in one embodiment, the indexing techniques provided herein result in improved acquisition of index sequence data through index diversity and permit accurate sequencing even for low-plexity sequencing runs.

To that end, FIG. 1 is a schematic illustration of an indexed nucleic acid fragment 12 of a sample according to the present techniques. The indexed nucleic acid fragment 12 represents a fragment suitable for a sequencing run. The indexed nucleic acid fragment 12 includes an insert 14 of nucleic acids derived from the sample, i.e., endogenous nucleic acids. The indexed nucleic acid fragment 12 also includes introduced or exogenous sequences that facilitate sequencing. Such sequences may include one or more sequencing primer sequences 16, 18 that are 5' and 3' of the insert 14 and that permit binding of universal sequencing primers to one or both strands. The indexed nucleic acid fragment 12 also includes a first index site 20 and a second index site 22. In the illustrated embodiment, the indexed nucleic acid fragment 12 also includes a first adapter sequence 26 and a second adapter sequence 28. The adapter sequence or sequences 26, 28 may be selected based on the desired sequencing platform and may be, for example, P7 and P5 adapters as illustrated, which facilitate flow cell or sequencing substrate attachment of the indexed nucleic acid fragment 12.

The illustrated indexed nucleic acid fragment 12 may be a double-stranded fragment and the first index sequence 20 may be located 5' of the insert 14 and the second index sequence 22 may be located 3' of the insert 14 in the forward strand such that the index sequences 20, 22 flank the insert. The first index sequence 20 is selected from a first index set 30, which includes a plurality (e.g., two, three, four, or more) index sequences, illustrated as index sequences 20a, 20b, 20c, 20d. The second index sequence 22, when present, is selected from a second index sequence, which includes a plurality of index sequences, illustrated as index sequences 22a, 22b, 22c, 22d.

Within the index set (e.g., index set 30 or index set 32), the individual index sequences (e.g., index sequence 20a, 20b, 20c, 20d) are different from one another. That is, they have different sequences from one another, as provided herein. Further, the index sequences in first index set 30 are also distinguishable from the index sequences in the second index set 32. In certain embodiments, the index sequences 20, 22 may distinguishable from the endogenous nucleic acids of the sample or samples. However, in other embodiments, the index sequences may not necessarily be distinguishable from the insert 14.

The index sequences may be single or double-stranded, and may be at least 5 bases, at least 6 bases, at least 7 bases, at least 8 bases, or more. In certain embodiments, the index sequences are 5-8 bases, 5-10 bases, 5-15 bases, 5-25 bases, 8-10 bases, 8-12 bases, 8-15 bases, or 8-25 bases in length, etc. Further, in certain embodiments, the index sequences (e.g., index sequences 20, 22) are no more than 30 bases, no more than 25 bases, no more than 20 bases, no more than 15 bases in length. It should be understood that the length of the index sequences as provided herein may refer to the unique/distinguishable portions of the sequences within each index set (and relative to other index sets) and may exclude adjacent common or universal sequences of the indexed nucleic acid fragment 12 that may serve as sequencing primers and that are common between all of the indexed nucleic acid fragments 12 from a sample.

While certain embodiments of the disclosed techniques are discussed in the context of dual-indexed sequencing techniques, it should be understood that the techniques provided herein may also be used in the context of single-indexed sequencing. For example, a nucleic acid fragment 12 may incorporate only one index sequence (e.g., index sequence 20 or 22) selected from an index set (e.g., index set 30). Further, the index sequences may be selected to be sequenced from one or both strands of a double-stranded nucleic acid fragment 12, e.g., in paired-end or single read sequencing, depending on the desired sequencing technique.

Figure 2:
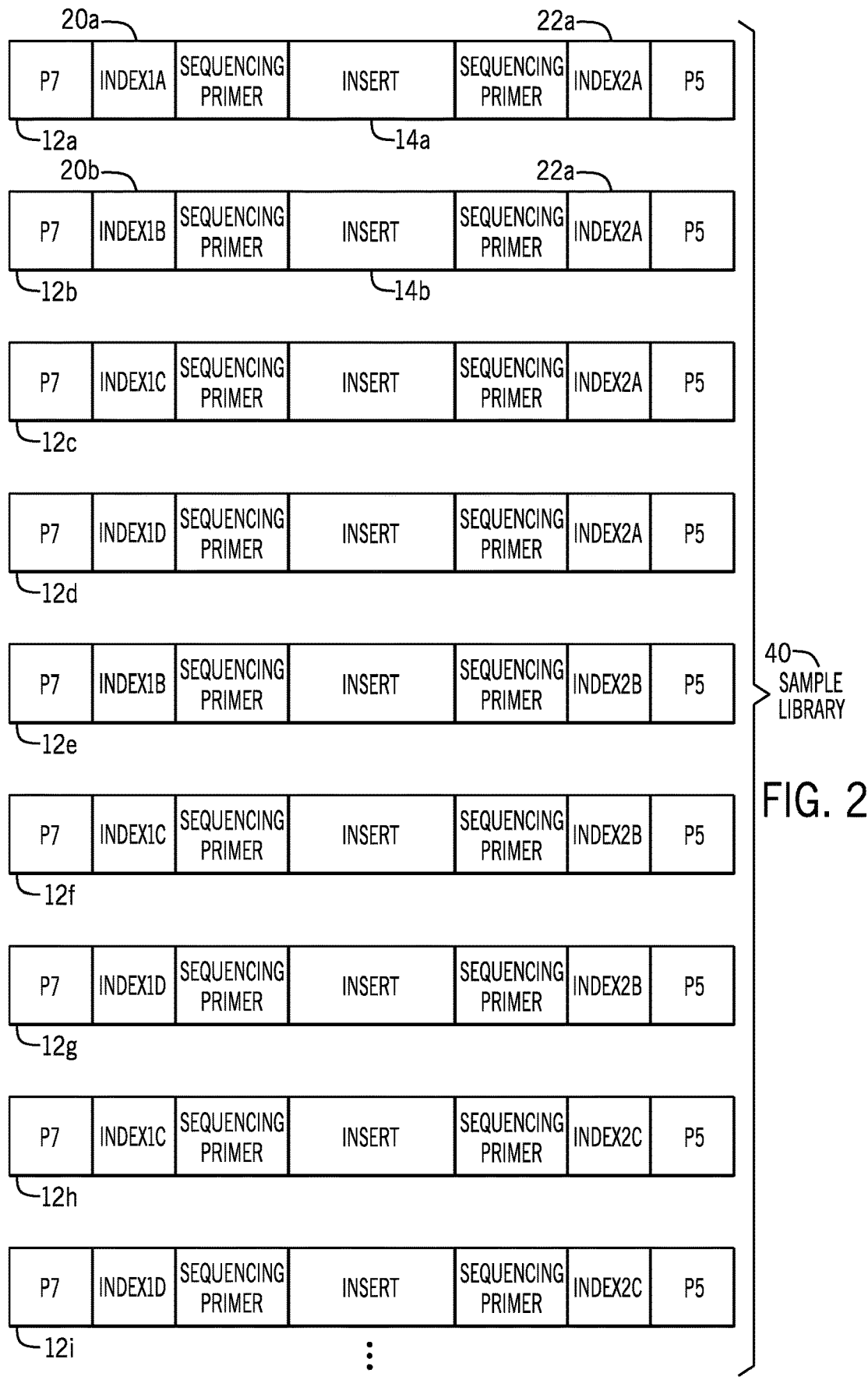
FIG. 2 is a schematic illustration of an indexed nucleic acid fragment library in accordance with the present techniques.

FIG. 2 is a schematic illustration of a sequencing library 40 derived from a sample and including indexed nucleic acid fragments 12. As illustrated, the library 40 has several different configurations of index combinations. For example, certain fragments 12a may be indexed with the combination of index 20a and index 22a, while other fragments 12b may be indexed with the combination of index 20b and 22a. It is contemplated that, during preparation of the library 40 from the sample, adapter mixtures including the different index sequences 20, 22 in each index set (e.g., the first index set 30 and the second index set 32) are used to modify the inserts 14 in a generally random fashion such that any given insert 14 may be modified with any one of an individual index sequence 20a, 20b, 20c, or 20d of first index set 30 and any one of individual index sequence 22a, 22b, 22c, or 22d of second index set 32. FIG. 2 shows a portion of the possible combinations of the first index sequence 20 and the second index sequence 22 that are present in the library. Further, it should be understood that additional combinations are possible, depending on the total number of index sequences in a particular index set used for the indexing. It should also be understood that, for a particular sample, multiple indexed nucleic acid fragments 12 with respective different inserts 14 will have the same configuration or combination of index sequences 20, 22.

Figure 3:
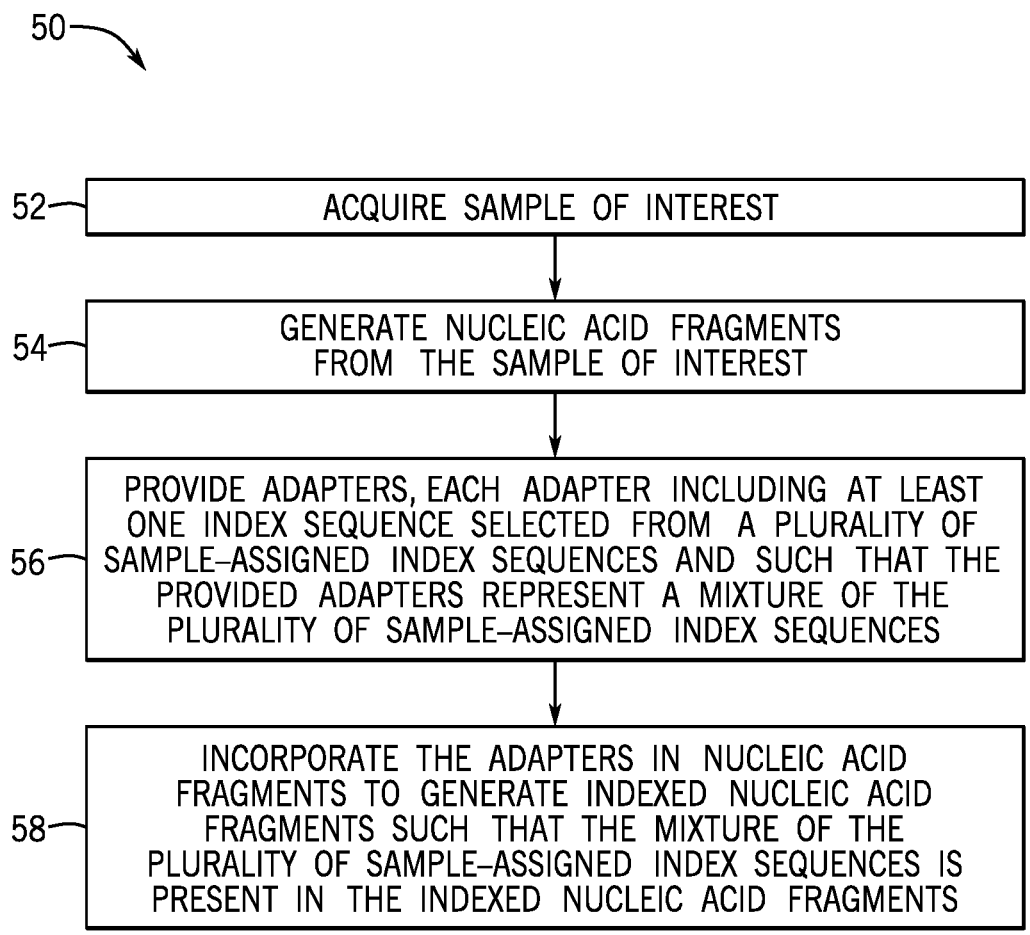
FIG. 3 is a flow diagram of methods of generating an indexed nucleic acid library of a sample in accordance with the present techniques.

FIG. 3 is a flow diagram of an embodiment of a method 50 for preparing the indexed library 40 of FIG. 2. After acquiring the sample of interest (step 52), the nucleic acids in the sample are fragmented (step 54). The fragmented nucleic acids are contact with a plurality of diverse index sequences of an index set. In particular, at the start of library preparation, one or more index sets may be associated with or assigned to a particular sample. The library preparation may then be prepared using only a sample-assigned index set or sets (step 56). In particular embodiments, the sample-assigned plurality of index sequences, e.g., the first index set 30 or the second index set 32, is provided with equal concentrations of each individual index sequence, e.g., index sequence 20, 22, in the set. That is, if the index set 30 has three different index sequences 20a, 20b, 20c, they are provided in a 1:1:1 ratio relative to one another and, in one embodiment, are provided as a mixture having equal concentrations (or approximately equal concentrations in a range of 0.9 to 1.1 relative to one another) of each index sequence 20.

Figure 4:
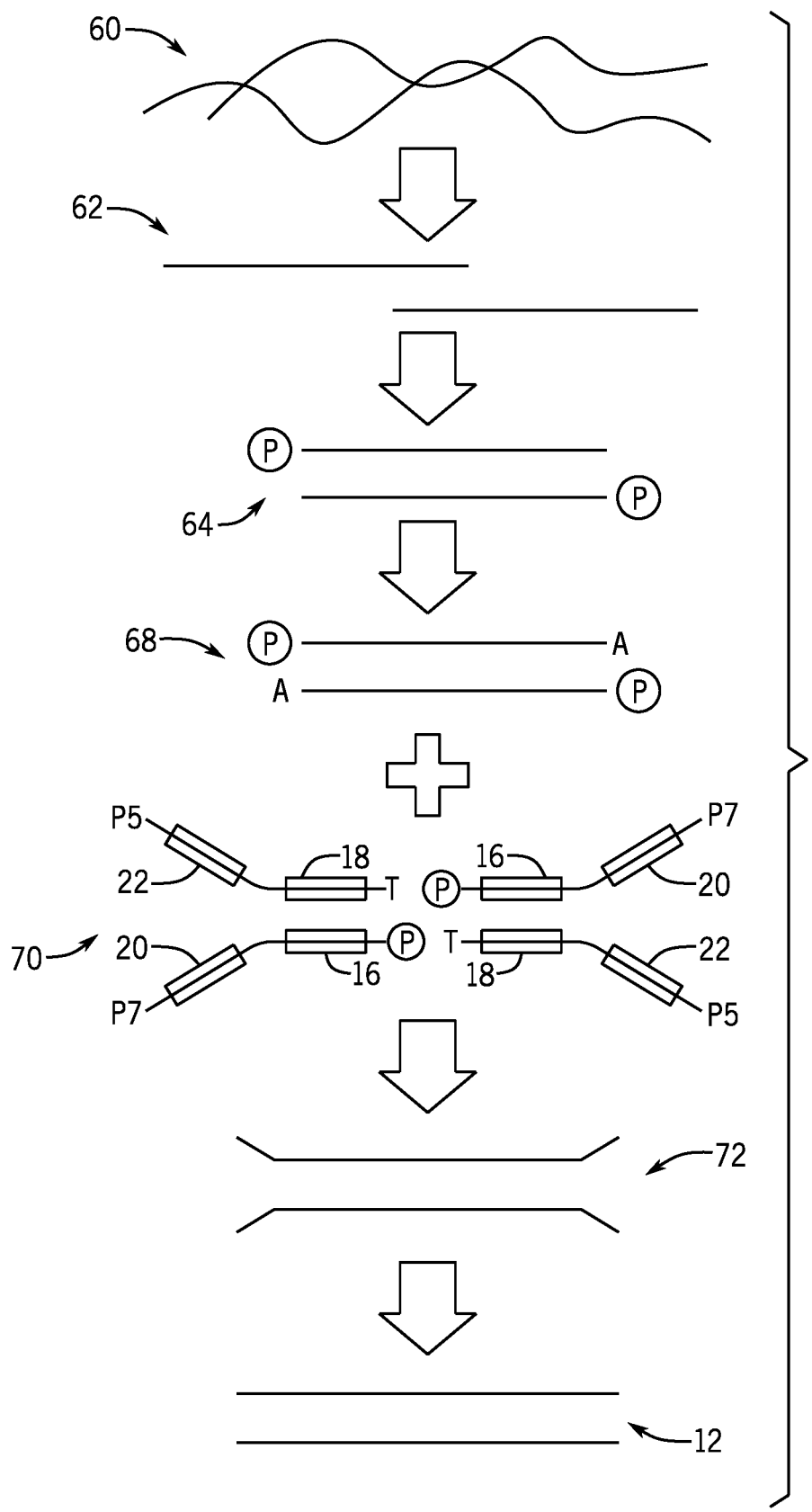
FIG. 4 is a flow diagram of methods of sequencing pooled indexed nucleic acid libraries in accordance with the present techniques.

The fragmented nucleic acids are modified with the adapters that include the sample-assigned index sequences (step 58) (e.g., as shown in FIG. 4). In other embodiments, the index sequences may be added to the fragmented nucleic acids in a separate step from adding the adapters. As a result of the modification, indexed nucleic acid fragments are generated. Providing the individual index sequences of each index set in substantially equal concentrations may facilitate relatively equal incorporation of each individual index sequence within the indexed nucleic acid fragments 12.

FIG. 4 is a schematic illustration of an embodiment of library preparation of a library of index nucleic acid fragments 12 from a sample 60. However, it should be understood that the illustrated method is by way of example and that the indexed nucleic acids 12 as provided herein may be prepared using other library preparation techniques e.g., tagmentation. In certain embodiments, the library is used to derive single-stranded template molecules that may be used in a sequencing reaction. The library may be formed from nucleic acids fragments with common sequences at their 5' and 3' ends but with diversity at one or more index sites and at an insert site. As explained in further detail below, the nucleic acid fragments within the library may contain regions of common sequence at (or proximal to) their 5' and 3' ends. In certain embodiments, the nucleic acid fragments of the library are "forked," such that a common sequence at the 5' end of each individual template in the library is not identical and not fully complementary to the common sequence at the 3' end of said template. However, in other embodiments, the adapters are not forked, e.g., are fully complementary.

The sample 60 is fragmented to generate fragmented nucleic acids 62 with overhanging ends that made blunt-ended by a number of methods known to those skilled in the art. In one method, the ends of the fragmented DNA are end repaired with T4 DNA polymerase and Klenow polymerase, and then phosphorylated with a polynucleotide kinase enzyme to generate phosphorylated fragmented nucleic acids 64. A single 'A' deoxynucleotide is then added to both 3' ends of the DNA molecules using Taq polymerase enzyme, producing a one-base 3' overhang fragmented nucleic acids 68 that are complementary to the one-base 3' 'T' overhang on the double-stranded end of the forked adapter.

A ligation reaction between a forked adapter 70 and one-base 3' overhang fragmented nucleic acids 68 is then performed using a suitable ligase enzyme (e.g. T4 DNA ligase) which joins two copies of the adapter to each DNA fragment, one at either end, to form adapter-target constructs 72. The products of this reaction can be purified from unligated adapter by a number of techniques, including size-inclusion chromatography, preferably by electrophoresis through an agarose gel slab followed by excision of a portion of the agarose that contains the DNA greater in size that the size of the adapter.

In particular, the depicted embodiment, the forked adapters 70 implemented in the library preparation include diverse index mixes at first index sequence 20 and the second index sequence 22. In contrast to other techniques in which the adapters coupled to the sample or insert nucleic acids are generally identical, the forked adapters 70 are prepared using a mix of the index sequences from index set 30 and index set 32, for example. Accordingly, the forked adapters 70 are not all identical to one another and are diverse on the basis of the particular combination of index sequences at the first index sequence 20 and the second index sequence 22. However, the sequencing primers 16, 18 and the adapter sequences are shared or common between the forked adapters 70. The adapter-target constructs 72 may be amplified to generate the indexed nucleic acid fragments 12, which in turn may be denatured to separate the double-stranded structure into single-stranded molecules prior to sequencing.

Figure 5:
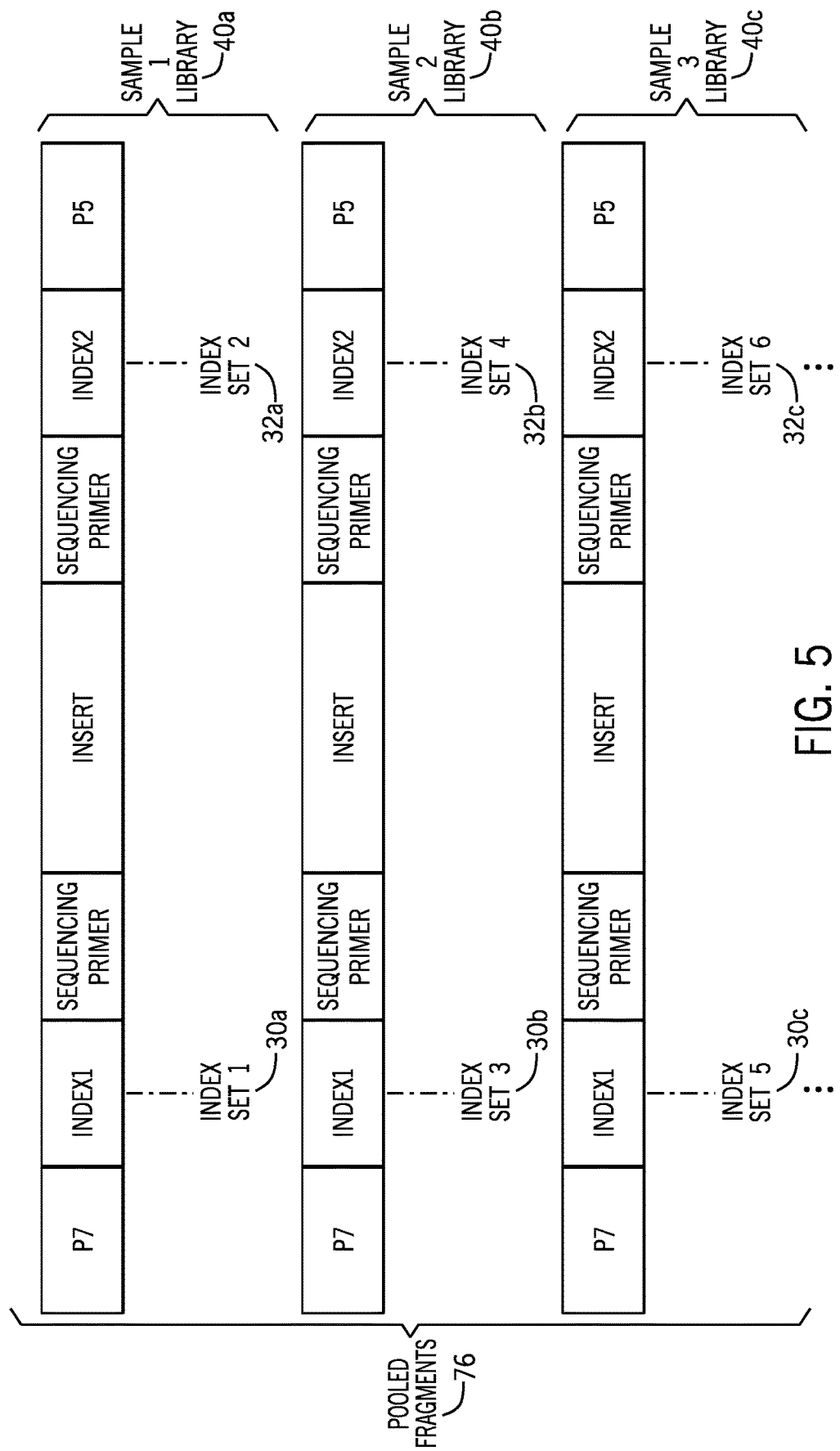
FIG. 5 is a schematic illustration of pooled indexed nucleic acid fragment libraries in accordance with the present techniques.

A library 40 of indexed nucleic acid fragments 12 may be prepared from a single sample and pooled with other libraries from other respective samples and prepared in a similar manner, according to the desired sequencing platform. FIG. 5 is a schematic illustration of libraries having dedicated or assigned different index sets 30, 32 that may be pooled and distinguished post-sequencing via the distinguishable index sequences present in the first index sets 30a, 30b, 30c, and/or the distinguishable index sequences present in the second index sets 32a, 32b, 32c. The first index set 30a, used in the creation of library 40a, includes a distinct set of index sequences that are not present and are non-overlapping with other index sets (30b, 32b, 30c, 32c) present in other libraries 40b, 40c. It should also be understood that the first index set 30a is also distinct from and non-overlapping with the second index set 32a used in the same library 40a.

Figure 6:
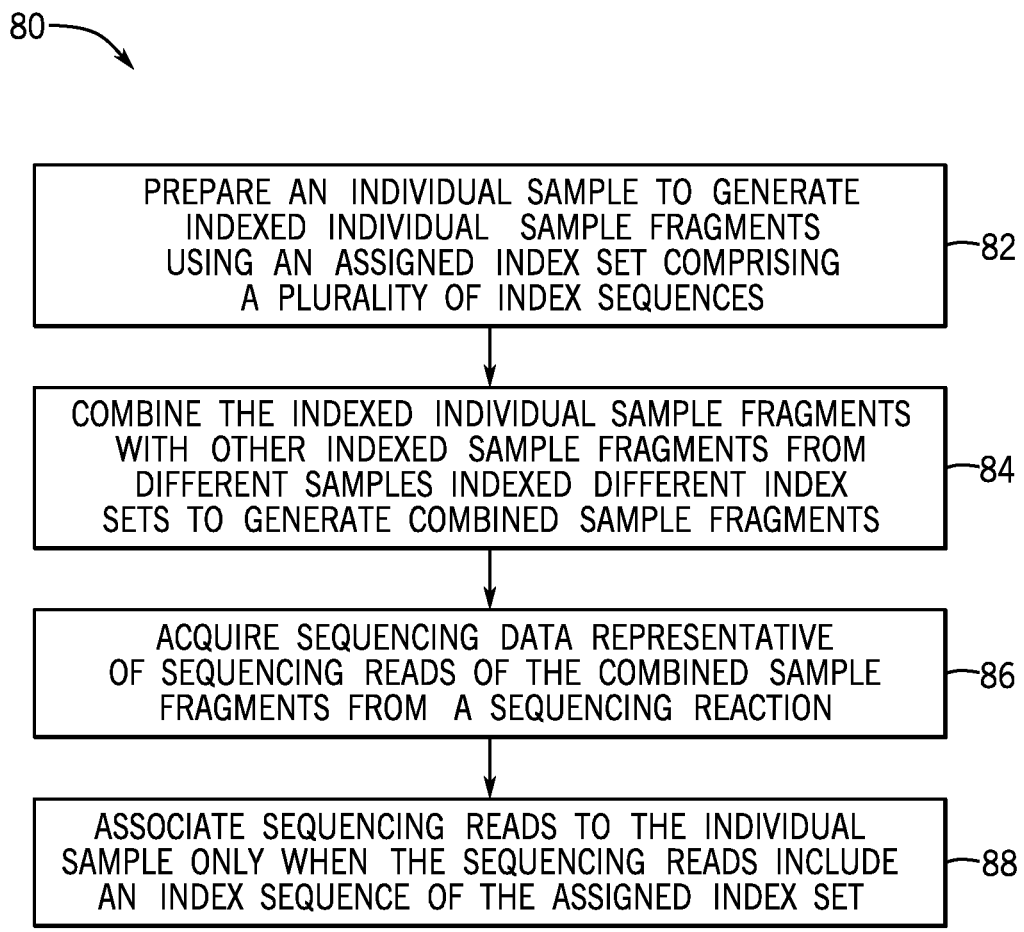
FIG. 6 is a schematic illustration of sequencing adapters including index sequences in accordance with the present techniques.

FIG. 6. is a flow diagram of a method 80 of sequencing pooled libraries from different samples (e.g., the libraries of FIG. 5) and using the index sequences as provided herein to assign sequencing data to the correct sample. At step 82, indexed individual sample fragments (e.g., indexed nucleic acid fragments 12) are prepared from an individual sample using at least one index set comprising a plurality of index sequences. The indexed individual sample fragments are pooled with other indexed sample fragments from different samples prepared using different (i.e., distinguishable from the indexes referred to in step 82) index sets to generate combined sample fragments at step 84. The pooling or combining may take place during sample loading onto a sequencing substrate. In one embodiment, the combined samples are loaded into different lanes of a flow cell. Because the lanes of the flow cell are separated from one another during a sequencing, the index sets used in the samples in a first lane of the flow cell may be used to index other samples in different lanes, so long as no samples within the same lane are indexed using the same index sets.

At step 86, sequencing data is acquired that is representative of sequencing of the combined sample fragments, and at step 88 sequencing reads are associated with the individual sample only when the sequencing reads include an index sequence of the assigned index set. In certain embodiments, when the indexed sample fragments each have a first index sequence and a second index sequence, a rules-based assignment requires that both the first index sequence and a second index sequence be members of the assigned index sets for a given sample. Failure at only one index site is sufficient to result in elimination of the sequencing read from downstream analysis (e.g., genome assembly) to eliminate reads with index hopping. In certain embodiments, the failed sequencing read may be stored for quality assessment. That is, certain potential index sequences may be associated with greater index failure, and these may be tracked for redesign.

Figure 7:
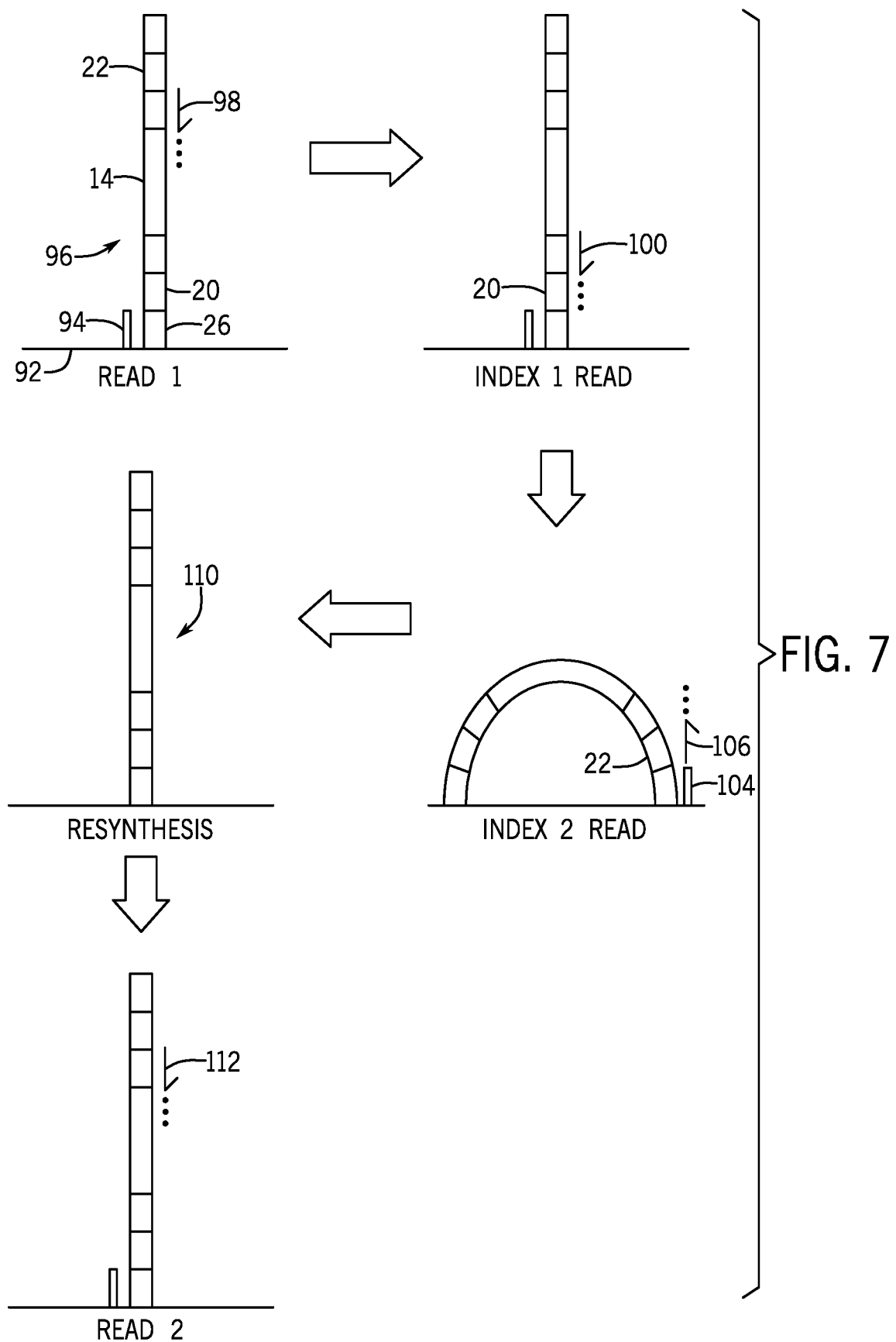
FIG. 7 is a flow diagram of methods of sequencing a nucleic acid library in accordance with the present techniques.

FIG. 7 is a schematic illustration of an embodiment of a sequencing technique 90 used to acquire sequencing data as provided herein. As illustrated, the sequenced nucleic acids are immobilized on a substrate 92 via a capture probe 94 complementary to the used in conjunction with a template strand 96 derived from denaturing the indexed nucleic acid fragments 12. The first sequencing read, read 1, is a sequence of the insert 14 that is acquired via contact with a read 1 primer 98 that targets (i.e., is complementary to) one of the sequencing primer sequences 16, 18. For example, if the template strand 96 is captured using the capture probe 94 complementary to a p7 (or other 5') adapter, the read 1 primer 98 may be complementary to the sequencing primer sequence 18.

After removal of the read 1 product, the technique 90 also may acquire a first index read of the index sequence 20 on the p7 side of the insert using a first index primer 100, which may be targeted to the sequencing primer 16 In the depicted embodiment, the first index read is on the same strand as read 1. While the read 1 read may be 100-150 bases, the index reads may be relatively shorter, e.g., 8-12 bases, or as long as a known length of the index sequences 20, 22. In this manner, sequencing resources are conserved. To acquire a second index read from the same strand after removal of the first index product, the template strand captured on the 3' end via a capture probe 104 may be used. For example, the second index read may be acquired with a second index read primer 106 targeting a portion of the p5 (or other 3') adapter or adjacent sequence. However, in other embodiments, the second index read may be acquired from a resynthesized complementary strand. After removal of the second index read product, a complementary strand 110 to template strand 96 is synthesized and the original template strand 96 is removed. Subsequently, the synthesized strand is contacted with a read 2 primer 112 to obtain a read 2 sequence that is a reverse complement of read 1 sequence. It is contemplated that the first index primer 100, the second index primer 106, and the read 1 and read 2 primers 98, 112 are universal to all template strands 96, regardless of template sample origin and index sequence. Based on the acquired first index and second index reads, the read 1 and read 2 sequencing data may be associated with a particular sample.

Figure 8:
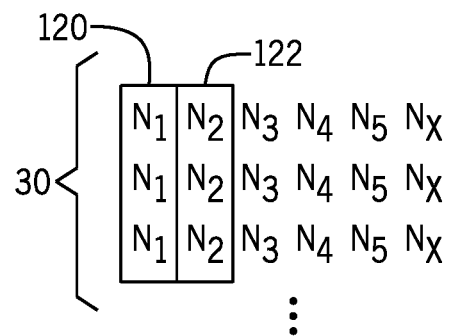
FIG. 8 is an example of an index set in accordance with the present techniques.
Figure 9:
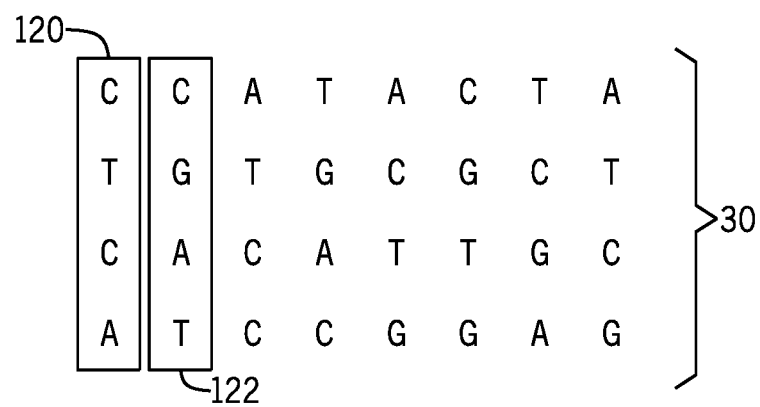
FIG. 9 is an example of an index set in accordance with the present techniques.

As provided herein, the index sets provide additional diversity for a given sample at the index read. When assigning a single index sequence to each sample, there is a risk that not all nucleotides will be represented in any given cycle of the index read when the number of samples is small. When that is done, the sequencing run may fail to generate usable data because the intensity correction and basecalling algorithms don't work as designed in the index cycles, which results in a failure to assign the reads to the samples. The most extreme example of this scenario is sequencing a single sample, which, for example, may be done for positive sample tracking and/or to remove non-indexed Phi X from the reads. A solution to this problem is to label each sample with multiple index sequences such that there is sufficient nucleotide representation for the primary analysis pipeline to work as designed. FIG. 8. is a representation of an index set (e.g., index set 30) with nucleotides $N_1$, $N_2$, etc. The index set may be selected such that, for any given position, the nucleotides are diverse within sequences of the index set. For example, at position 120, the nucleotides may be different such that three or more of A, C, T, and G are represented across the index set. In FIG. 9, which depicts a specific embodiment of an index set 30, three different nucleotides are represented at position 120 and four different nucleotides are represented at position 122. Accordingly, the index sets may be designed such that, at each nucleotide position, at least three different nucleotides are represented across the index set. In other embodiments, four different nucleotides are represented across the index set at at least half of the nucleotide positions in the index sequence. Further, in certain embodiments, the index sequences are internally diverse. That is, at least a portion of adjacent nucleotides of an individual index sequence are different from one another.

Further, certain indices may not perform as well as others, which results in certain samples being under-represented even if the concentration of the samples input is identical. A benefit of placing multiple index sequences on each sample is that the overall impact of poor performance of one index sequence is limited. Within this strategy, it is also possible to group high and low performing index sequences together, to further improve uniformity of representation across different samples.

Table 1 and Table 2 are examples of index sets (e.g., index set 30, 32) and the individual index sequences (e.g., index sequence 20, 22) that make up an index set according to the present techniques. For example, the index sequences (e.g., index sequences 20, 22) under each individual Group # are contemplated as being a single index set. That is, Group #0 includes four different index sequences F7-001, F7-002, F7-003, and F7-004 that together form a single index set. Group #1 includes an additional four different index sequences F7-005, F7-006, F7-007, and F7-008 that together form a single index set, and so on.

In the index sets shown below, four indices are present per index set. However, it should be understood that the size of the index set may vary and may include three, four, or more individual distinguishable index sequences. The index sets shown were selected to ensure that within any group, there is balanced representation of nucleotides. Specifically, within any group, the second least frequent nucleotide in each cycle must be present in at least 25% of index sequences.

Table 1 shows index sets that may be a P7-side index set 30. However, in certain embodiments, the sequences in Table 1 may be used on the P5 side as the index set 32.

TABLE 1

| P7 Index Sets |
| --- |
| Index group #0 |
| F7-001, CCATACTA |
| F7-002, TGTGCGCT |
| F7-003, CACATTGC |
| F7-004, ATCCGGAG |
| Index group #1 |
| F7-005, ACCTTAAC |
| F7-006, CAGCGCCT |

TABLE 1-continued

| P7 Index Sets |
| --- |
| F7-007, TGAACAGG |
| F7-008, GTGGCTCA |
| Index group #2 |
| F7-009, GGTAACAC |
| F7-010, TTCTGATG |
| F7-011, ACGCTTGT |
| F7-012, GAATAGCA |
| Index group #3 |
| F7-013, GGATTCAA |
| F7-014, ATTGAACT |
| F7-015, TCCAAGGC |
| F7-016, TAACCTTG |
| Index group #4 |
| F7-017, GAGACAAC |
| F7-018, TGTTAGGA |
| F7-019, ACAGTATG |
| F7-020, CTTCTTCT |
| Index group #5 |
| F7-021, GTCGCCTT |
| F7-022, CGGTGAGA |
| F7-023, TCACTGAA |
| F7-024, AGCAATTG |
| Index group #6 |
| F7-025, TAGGTTGA |
| F7-026, CCTTCGCC |
| F7-027, GGATAATG |
| F7-028, TTCACAAT |
| Index group #7 |
| F7-029, TGGCACGG |
| F7-030, ATATCTAC |
| F7-031, GCTCGGTT |
| F7-032, CTAATGTA |
| Index group #8 |
| F7-033, AAGATGAA |
| F7-034, GCCGAATC |
| F7-035, AGATGCGG |
| F7-036, TTCCATCC |

TABLE 1-continued

P7 Index Sets

Index group #9
F7-037, CCTCACGT
F7-038, GTGTGGAC
F7-039, TCCGTTCG
F7-040, TGAGGATA

Index group #10
F7-041, TGATTGCC
F7-042, AACAGCTT
F7-043, CATCATAA
F7-044, TTGTCAGC

Index group #11
F7-045, CGGAACTT
F7-046, GTACTTGG
F7-047, AACGCACC
F7-048, GCTTAGAG

Index group #12
F7-049, TAATCGAT
F7-050, CCGGTCCA
F7-051, ATTAGTTC
F7-052, CGCGAAGG

Index group #13
F7-053, CTCTAGCT
F7-054, TCGATCTG
F7-055, AATGGAGA
F7-056, CGGCCTAT

Index group #14
F7-057, TGCCTCTT
F7-058, CCAGCTGC
F7-059, AAGTGTCA
F7-060, GTTATACG

Index group #15
F7-061, GTAGAGGC
F7-062, TAGTCCTA
F7-063, CCTAGAAT
F7-064, GACCTCCG Table 2 shows index sets that may be a P5-side index set 32. In certain embodiments, the index sets are designed to be used in conjunction with the P7 index set 30 having the same group number to generate indexed nucleic acid fragments for a sample. For example, certain paired sets may have completed quality assessment when in use together and may be associated with low levels of index hopping or generally evenly distributed amplification yields. In other embodiments, any given P7-side (or 5'-side) index set 30 may be used with any another P5-side index set 32.

P5 Index Sets

Index group #0
F5-001, TCGCTCTA
F5-002, ATTGGAGG
F5-003, AACTAGAC
F5-004, CGGACTAT

Index group #1
F5-005, TCCTTAGG
F5-006, AGGAGGAA
F5-007, CAACACTC
F5-008, GTGGTTCT

Index group #2
F5-009, TGGTGGTT
F5-010, GCTACCGC
F5-011, AGCGTTCA
F5-012, CAATTATG

Index group #3
F5-013, TTACAAGA
F5-014, GGTTCTAC
F5-015, ACGTGGCG
F5-016, CACAATTG

Index group #4
F5-017, CCATTCAA
F5-018, TAGCAGGC
F5-019, TTCAGATG
F5-020, AGTGCGGT

Index group #5
F5-021, ATTCAACT
F5-022, TCAAGGAG
F5-023, CACCTCGA
F5-024, AGGTATCC

Index group #6
F5-025, AAGCGCTT
F5-026, TGTGTAGC
F5-027, CTATAGAG
F5-028, GCCACTTA P5 Index Sets Index group #7

F5-029, TGTCCTTG

F5-030, AACATGGT

F5-031, GTGTGCAA

F5-032, CCTGAACA

Index group #8

F5-033, CTTCTTGC

F5-034, TAGGAATA

F5-035, AGTTGCCT

F5-036, TCCACAAT

Index group #9

F5-037, AGACCTCT

F5-038, CTCATGTA

F5-039, CCGTACGC

F5-040, GAAGGTCG

Index group #10

F5-041, AGATTGAT

F5-042, TCTGATTC

F5-043, ATCCGCCA

F5-044, GAGACGAG

Index group #11

F5-045, CGCTAACT

F5-046, ATAGCTAG

F5-047, GCACTGGC

F5-048, TCGAGCGT

Index group #12

F5-049, GGCAAGTT

F5-050, CTGTTCCG

F5-051, ACCGGTGC

F5-052, GATCCATA

Index group #13

F5-053, TTCACTCC

F5-054, ACTTACTA

F5-055, GAAGCAAT

F5-056, GGTCGTGA

Index group #14

F5-057, GCCGTCAT

F5-058, TGTCGGCC

P5 Index Sets

F5-059, ATGAATGG

F5-060, CATGGATT

Index group #15

F5-061, AGCCTAAG

F5-062, CAAGCTGA

F5-063, GTGTAATT

F5-064, TGTAACAC

Figure 10:
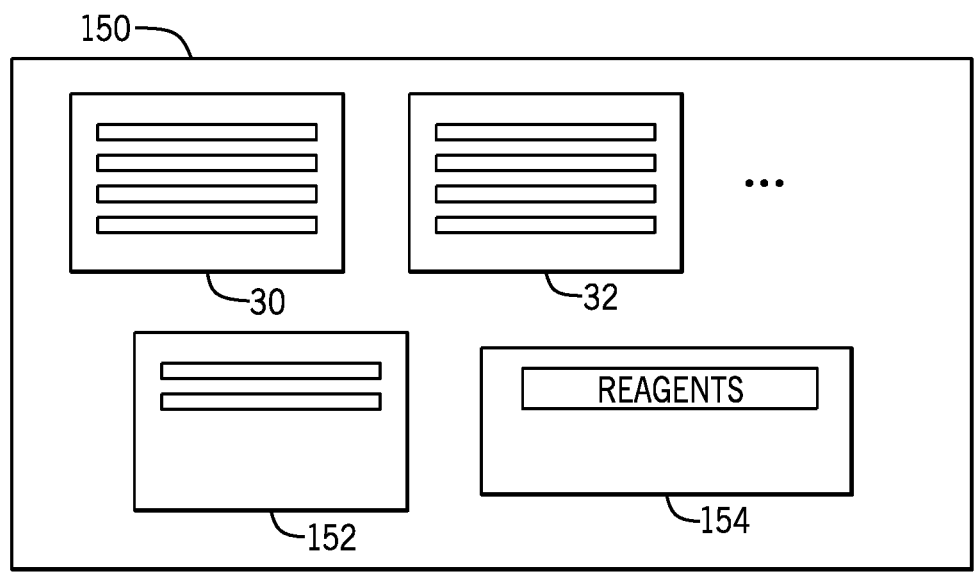
FIG. 10 is a nucleic acid sequencing kit in accordance with the present techniques.

FIG. 10 is an example of a sample preparation kit 150 for sequencing that may be used in conjunction with the present techniques, i.e., to prepare indexed nucleic acid fragments 12 from an individual sample and, in certain embodiments, to sequence the indexed nucleic acid fragments 12. The sample preparation kit 150 may include a first index set 30 and, when used, a second index set 32. In certain embodiments, the first index set 30 and/or the second index set 32 may be provided in the form of adapter nucleic acids that include additional elements, such as primer sequences, adapter sequences, etc. The first index set 30 and/or the second index set 32 may be provided within respective individual containers in premixed quantities such that each individual index sequence is present in approximately equal concentrations and such that the index diversity for a given sample is not as susceptible to user error. In embodiments in which the adapters are forked dual-indexed adapters, both index sets 30, 32 may be present in a single adapter nucleic acid, which may be provided in a single container. The sample preparation kit 150 may also include the appropriate primers 152 for use in conjunction with the desired sequencing platform. The sample preparation kit 150 may also include one or more sample preparation enzymes, buffers, and/or reagents 154. The sample preparation kit 150 may be provided as a prepackaged kit for preparing a library from a single sample or, in certain embodiments, may be provided as a multi-sample kit with a plurality of different index sets 30, 32.

Figure 11:
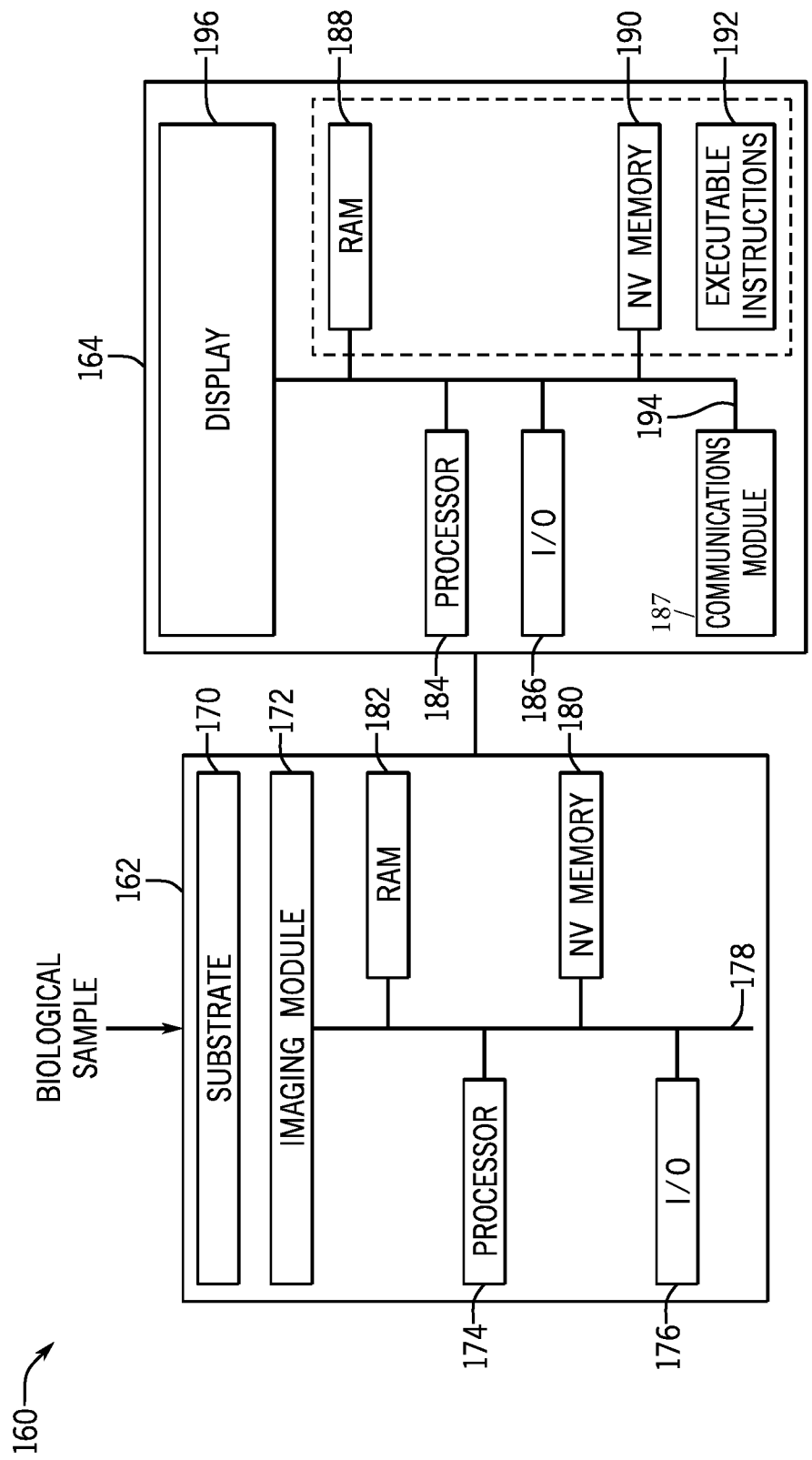
FIG. 11 is a block diagram of a sequencing device configured to acquire sequencing data in accordance with the present techniques.

FIG. 11 is a schematic diagram of a sequencing device 160 that may be used in conjunction with the disclosed embodiments for acquiring sequencing data from indexed nucleic acids (e.g., sequencing reads, read 1, read 2, index reads, index read 1, index read 2, multi-sample sequencing data) that assigned to individual samples using the indexing techniques as provided herein. The sequence device 160 may be implemented according to any sequencing technique, such as those incorporating sequencing-by-synthesis methods described in U.S. Patent Publication Nos. 2007/0166705; 2006/0188901; 2006/0240439; 2006/0281109; 2005/0100900; U.S. Pat. No. 7,057,026; WO 05/065814; WO 06/064199; WO 07/010251, the disclosures of which are incorporated herein by reference in their entireties. Alternatively, sequencing by ligation techniques may be used in the sequencing device 160. Such techniques use DNA ligase to incorporate oligonucleotides and identify the incorporation of such oligonucleotides and are described in U.S. Pat. Nos. 6,969,488; 6,172,218; and 6,306,597; the disclosures of which are incorporated herein by reference in their entireties. Some embodiments can utilize nanopore sequencing, whereby target nucleic acid strands, or nucleotides exonucleolytically removed from target nucleic acids, pass through a nanopore. As the target nucleic acids or nucleotides pass through the nanopore, each type of base can be identified by measuring fluctuations in the electrical conductance of the pore (U.S. Pat. No. 7,001,792; Soni & Meller, *Clin. Chem.* 53, 1996-2001 (2007); Healy, *Nanomed.* 2, 459-481 (2007); and Cockroft, et al. *J. Am. Chem. Soc.* 130, 818-820 (2008), the disclosures of which are incorporated herein by reference in their entireties). Yet other embodiments include detection of a proton released upon incorporation of a nucleotide into an extension product. For example, sequencing based on detection of released protons can use an electrical detector and associated techniques that are commercially available from Ion Torrent (Guilford, CT, a Life Technologies subsidiary) or sequencing methods and systems described in US 2009/0026082 A1; US 2009/0127589 A1; US 2010/0137143 A1; or US 2010/0282617 A1, each of which is incorporated herein by reference in its entirety. Particular embodiments can utilize methods involving the real-time monitoring of DNA polymerase activity. Nucleotide incorporations can be detected through fluorescence resonance energy transfer (FRET) interactions between a fluorophore-bearing polymerase and γ-phosphate-labeled nucleotides, or with zeromode waveguides as described, for example, in Levene et al. *Science* 299, 682-686 (2003); Lundquist et al. *Opt. Lett.* 33, 1026-1028 (2008); Korlach et al. *Proc. Natl. Acad. Sci. USA* 105, 1176-1181 (2008), the disclosures of which are incorporated herein by reference in their entireties. Other suitable alternative techniques include, for example, fluorescent in situ sequencing (FISSEQ), and Massively Parallel Signature Sequencing (MPSS). In particular embodiments, the sequencing device 160 may be a HiSeq, MiSeq, or HiScanSQ from Illumina (La Jolla, CA). In other embodiment, the sequencing device 160 may be configured to operate using a CMOS sensor with nanowells fabricated over photodiodes such that DNA deposition is aligned one-to-one with each photodiode.

The sequencing device 160 may be "one-channel" a detection device, in which only two of four nucleotides are labeled and detectable for any given image. For example, thymine may have a permanent fluorescent label, while adenine uses the same fluorescent label in a detachable form. Guanine may be permanently dark, and cytosine may be initially dark but capable of having a label added during the cycle. Accordingly, each cycle may involve an initial image and a second image in which dye is cleaved from any adenines and added to any cytosines such that only thymine and adenine are detectable in the initial image but only thymine and cytosine are detectable in the second image. Any base that is dark through both images in guanine and any base that is detectable through both images is thymine. A base that is detectable in the first image but not the second is adenine, and a base that is not detectable in the first image but detectable in the second image is cytosine. By combining the information from the initial image and the second image, all four bases are able to be discriminated using one channel.

In the depicted embodiment, the sequencing device 160 includes a separate sample processing device 162 and an associated computer 164. However, as noted, these may be implemented as a single device. Further, the associated computer 164 may be local to or networked with the sample processing device 162. In the depicted embodiment, the biological sample may be loaded into the sample processing device 162 on a sample substrate 170, e.g., a flow cell or slide, that is imaged to generate sequence data. For example, reagents that interact with the biological sample fluoresce at particular wavelengths in response to an excitation beam generated by an imaging module 172 and thereby return radiation for imaging. For instance, the fluorescent components may be generated by fluorescently tagged nucleic acids that hybridize to complementary molecules of the components or to fluorescently tagged nucleotides that are incorporated into an oligonucleotide using a polymerase. As will be appreciated by those skilled in the art, the wavelength at which the dyes of the sample are excited and the wavelength at which they fluoresce will depend upon the absorption and emission spectra of the specific dyes. Such returned radiation may propagate back through the directing optics. This retrobeam may generally be directed toward detection optics of the imaging module 172.

The imaging module detection optics may be based upon any suitable technology, and may be, for example, a charged coupled device (CCD) sensor that generates pixilated image data based upon photons impacting locations in the device. However, it will be understood that any of a variety of other detectors may also be used including, but not limited to, a detector array configured for time delay integration (TDI) operation, a complementary metal oxide semiconductor (CMOS) detector, an avalanche photodiode (APD) detector, a Geiger-mode photon counter, or any other suitable detector. TDI mode detection can be coupled with line scanning as described in U.S. Pat. No. 7,329,860, which is incorporated herein by reference. Other useful detectors are described, for example, in the references provided previously herein in the context of various nucleic acid sequencing methodologies.

The imaging module 172 may be under processor control, e.g., via a processor 174, and the sample receiving device 162 may also include I/O controls 176, an internal bus 178, non-volatile memory 180, RAM 182 and any other memory structure such that the memory is capable of storing executable instructions, and other suitable hardware components that may be similar to those described with regard to FIG. 11. Further, the associated computer 164 may also include a processor 184, I/O controls 186, a communications module 194, and a memory architecture including RAM 188 and non-volatile memory 190, such that the memory architecture is capable of storing executable instructions 192. The hardware components may be linked by an internal bus 194, which may also link to the display 196. In embodiments in which the sequencing device 160 is implemented as an all-in-one device, certain redundant hardware elements may be eliminated.

The processor 184 may be programmed to assign individual sequencing reads to a sample based on the associated index sequence or sequences according to the techniques provided herein. In particular embodiments, based on the image data acquired by the imaging module 172, the sequencing device 160 may be configured to generate sequencing data that includes base calls for each base of a sequencing read. Further, based on the image data, even for sequencing reads that are performed in series, the individual reads may be linked to the same location via the image data and, therefore, to the same template strand. In this manner, index sequencing reads may be associated with a sequencing read of an insert sequence before being assigned to a sample of origin. The processor 184 may also be programmed to perform downstream analysis on the sequences corresponding to the inserts for a particular sample subsequent to assignment of sequencing reads to the sample.

Figure 12:
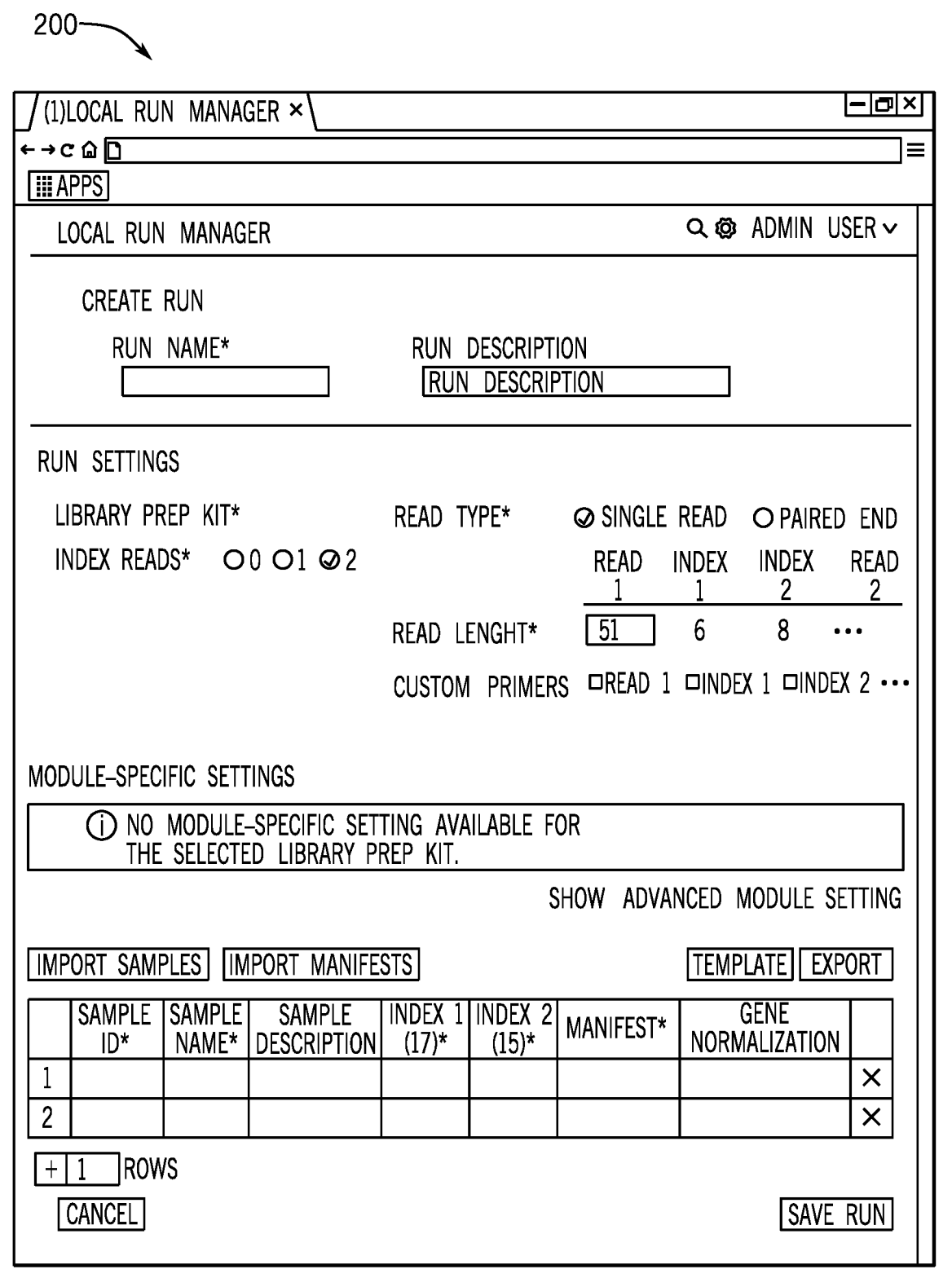

FIG. 12 is an example of a graphical user interface screen 200 that may be generated by the sequencing device 160 for user input of information related to sequencing reactions using the indexed nucleic acid fragments as provided herein. For example, the user may provide input relating to a name or identification of each sample in the sequencing run, the number if index sites, and the particular index set or sets used for each sample. In one embodiment, the index sets are commercially available and the user interface screen 200 provides a drop-down menu of commercially available index sets. Each individual sample may then be associated with a selected one or more commercially available index sets. Based on the selection, the processor (e.g., processor 184) of the sequencing device 160 accesses stored index sequence information corresponding to the selected index set from a memory and uses the accessed index sequence information to assign index sequence reads acquired by the sequencing device 160 to particular samples. Once assigned to a particular sample based on the index sequence read or reads, sequencing reads representative of the insert and associated with an imaged location of the index sequence read are co-assigned to the particular sample.

Technical effects of the disclosed embodiments include improved and more accurate indexing of nucleic acid sequences. Improved indexing may reduce incorrectly assigned sequencing reads from a multiplexed (e.g., multi-sample) to more meaningful information to clinicians. Further, the improvements in accuracy of sequencing read assignment associated with the present techniques facilitate high throughput sequencing strategies that provide commercial and time savings. The index sequences as provided herein address bias introduced into sequencing data that affects sequencing coverage counts.

While only certain features of the disclosure have been illustrated and described herein, many modifications and changes will occur to those skilled in the art. It is, therefore, to be understood that the appended claims are intended to cover all such modifications and changes as fall within the true spirit of the disclosure.

The invention claimed is:

1. A sample-indexed nucleic acid library preparation, comprising: a first nucleic acid library prepared from a first sample, wherein the first nucleic acid library comprises a first plurality of nucleic acid fragments, wherein each nucleic acid fragment of the first plurality comprises at least two different index sequences selected from a first set of index sequences that are all distinguishable from one another, the first set of index sequences comprising a first 5' subset and a first 3' subset, wherein the first set of index sequences are arranged on individual nucleic acid fragments of the first plurality such that index sequences of the first 5' subset are located 5' of a target sequence and not 3' of the target sequence, and index sequences of the first 3' subset are located 3' of the target sequence and not 5' of the target sequence, wherein the first plurality comprises more than one combination of the two different index sequences such that one or more individual fragments of the first plurality of nucleic acid fragments have respective different 5' index sequences and respective different 3' index sequences relative to one another, wherein more than one fragment of the first plurality has a same combination of the two different index sequences and different target sequences, and wherein the same combination comprises an index sequence of the first 5' subset and an index sequence of the first 3' subset; and a second nucleic acid library prepared from a second sample, wherein the second nucleic acid library comprises a second plurality of nucleic acid fragments, wherein each nucleic acid fragment of the second plurality comprises at least two different index sequences selected from a second set of unique index sequences that are all distinguishable from one another and from the first set of index sequences, the second set of unique index sequences comprising a second 5' subset and a second 3' subset, wherein the second set of index sequences are arranged on individual nucleic acid fragments of the second plurality such that index sequences of the second 5' subset are located 5' of a target sequence and not 3' of the target sequence and index sequences of the second 3' subset are located 3' of the target sequence and not 5' of the target sequence wherein the first set of index sequences are associated with the first sample and not the second sample and wherein the second set of index sequences are associated with the second sample and not the first sample, wherein the second plurality comprises more than one combination of the two different index sequences such that one or more individual fragments of the second plurality of nucleic acid fragments have respective different 5' index sequences and respective different 3' index sequences relative to one another, and wherein more than one fragment of the second plurality has a same combination of the two different index sequences and different target sequences, wherein the same combination comprises an index sequence of the second 5' subset and an index sequence of the second 3' subset.

2. The library preparation of claim 1, wherein:
(i) the first plurality of nucleic acid fragments comprises individual nucleic acid fragments having different combinations of the at least two different index sequences from the first set of index sequences relative to other individual nucleic acid fragments within the first plurality of nucleic acid fragments; and/or
(ii) the second plurality of nucleic acid fragments comprises individual nucleic acid fragments having different combinations of the at least two different index sequences from the second set of index sequences relative to other individual nucleic acid fragments within the second plurality of nucleic acid fragments.

3. The library preparation of claim 1, wherein each index sequence of the first set of index sequences is present in the first plurality of nucleic acid fragments and at a ratio relative to the other index sequences in the first set of index sequences between 0.9 to 1.1, or wherein each index sequence of the first set of index sequences is present in the first plurality of nucleic acid fragments at approximately equal concentrations.

4. The library preparation of claim 1, wherein each index sequence of the second set of index sequences is present in the second plurality of nucleic acid fragments and at a ratio relative to the other index sequences in the second set of index sequences between 0.9 to 1.1, or wherein each index sequence of the second set of index sequences is present in the second plurality of nucleic acid fragments at approximately equal concentrations.

5. The library preparation of claim 1, wherein the first sample and the second sample are nucleic acid samples from different individuals.

6. The library preparation of claim 1, wherein an individual nucleic acid fragment of the first plurality of nucleic acid fragments comprises only one index sequence of the first 5' subset and only one index sequence of the first 3' subset.

7. The library preparation of claim 1, wherein individual nucleic acid fragments of the first plurality of nucleic acid fragments comprise different combinations of the at least two different index sequences relative to one another.

8. The library preparation of claim 1, wherein the second 5' subset comprises four or more unique index sequences.

9. The library preparation of claim 8, wherein an individual nucleic acid fragment of the second plurality of nucleic acid fragments comprises only one index sequence of the second 5' subset and only one index sequence of the second 3' subset.

10. The library preparation of claim 1, wherein at each nucleotide position within the first 5' subset, at least three different nucleotides are represented.

11. The library preparation of claim 1, wherein, for the first 5' subset, at least 50% of nucleotide positions across the first 5' subset, four different nucleotides are present across the first plurality.

12. The library preparation of claim 1, wherein the first 5' subset comprises four or more different index sequences and the first 3' subset comprises four or more different index sequences and wherein the second 5' subset comprises four or more different index sequences and the second 3' subset comprises four or more different index sequences.

13. The library preparation of claim 1, wherein first plurality of nucleic acid fragments and the second plurality of nucleic acid fragments are single-stranded nucleic acids.

14. The library preparation of claim 1, wherein the first 5' subset comprises three or four different index sequences.

15. The library preparation of claim 1, wherein an individual index of the first 5' subset is present in different fragments of the first plurality and combined with respective different indexes of the first 3' subset.

16. The library preparation of claim 1, wherein an individual index of the first 3' subset is present in different fragments of the first plurality and combined with respective different indexes of the first 5' subset.

17. A sample-indexed nucleic acid library preparation, comprising:

a first nucleic acid library prepared from a first sample, wherein the first nucleic acid library comprises a first plurality of dual-indexed nucleic acid fragments having respective different target sequences, wherein the first nucleic acid library comprises a first sample 5' set of different 5' index sequences and a first sample 3' set of different 3' index sequences, and wherein each nucleic acid fragment of the first plurality comprises a 5' index sequence selected from the first sample 5' set and a 3' index selected from the first sample 3' set, and wherein the different 5' index sequences and the different 3' index sequences are randomly combined among the first plurality of dual-indexed nucleic acid fragments such that a plurality of possible combinations of the 5' index sequence and the 3' index sequence are represented in the first nucleic acid library and wherein at least one possible combination is present in more than one fragment of the first nucleic acid library; and a second nucleic acid library prepared from a second sample, wherein the second nucleic acid library comprises a second plurality of dual-indexed nucleic acid fragments having respective different target sequences, wherein the second nucleic acid library comprises a second sample 5' set of different 5' index sequences and a second sample 3' set of different 3' index sequences, and wherein each nucleic acid fragment of the second plurality comprises a 5' index sequence selected from the second sample 5' set and a 3' index selected from the second sample 3' set, and wherein the different 5' index sequences and the different 3' index sequences are randomly combined among the second plurality of dual-indexed nucleic acid fragments such that a plurality of possible combinations of the 5' index sequence and the 3' index sequence are represented in the second nucleic acid library, wherein at least one possible combination is present in more than one fragment of the second nucleic acid library, and wherein the first sample 5' set of different 5' index sequences, the first sample 3' set of different 3' index sequences, the second sample 5' set of different 5' index sequences and the second sample 3' set of different 3' index sequences are all distinguishable from one another.

18. The sample-indexed nucleic acid library preparation of claim 17, wherein all possible combinations of the 5' index sequence and the 3' index sequence are represented in the first nucleic acid library.

19. The sample-indexed nucleic acid library preparation of claim 17, wherein all possible combinations of the 5' index sequence and the 3' index sequence are represented in the second nucleic acid library.

* * * * *